United States Patent [19]

Shirosaki et al.

[11] 4,450,279
[45] May 22, 1984

[54] DIALKYLTHIOXANTHONES

[75] Inventors: Tsutomu Shirosaki, Tokyo; Seiki Fukunaga, Yono, both of Japan

[73] Assignee: Nippon, Kayaku, Kabushiki, Kaisha, Tokyo, Japan

[21] Appl. No.: 354,230

[22] Filed: Mar. 2, 1982

[30] Foreign Application Priority Data

Mar. 16, 1981 [JP] Japan ................................. 56-36493

[51] Int. Cl.³ ........................................ C07D 335/16
[52] U.S. Cl. ..................................................... 549/27
[58] Field of Search .......................................... 549/27

[56] References Cited

U.S. PATENT DOCUMENTS 3,759,807  9/1973  Osborn et al. ................. 204/159.23
3,926,643  12/1975  Chang ......................... 05001975/90

FOREIGN PATENT DOCUMENTS 36075A   9/1981  European Pat. Off. .
2811755  9/1978  Fed. Rep. of Germany .
55-105678  8/1980  Japan .

OTHER PUBLICATIONS

Chem. Abstracts, vol. 96, 219374r, (pp. 94–95).

Protiva et al., Chemical Abstracts, vol. 64, (1966), 17551d.

Primary Examiner—Richard Raymond

[57] ABSTRACT

The present invention relates to a dialkylthioxanthone compound of formula (I):

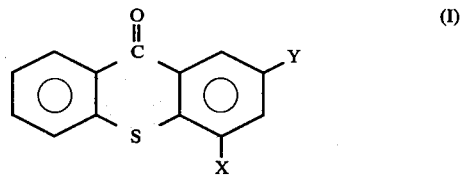

wherein X and Y may be the same or different, and represent a straight-chain or branched alkyl group having 1–12 carbon atoms with a proviso that sum of carbon atoms of alkyl groups X and Y is in the range of 3–15; a process for producing said compound; a process for hardening a photopolymerizable resin compound having an ethylenically unsaturated double bond which is radically crosslinkable or polymerizable using the above compound; and a photopolymerizable resin composition containing the same.

4 Claims, No Drawings

DIALKYLTHIOXANTHONES

DETAILED DESCRIPTION OF THE INVENTION

The present invention relates to a dialkylthioxanthone compound of formula (I):

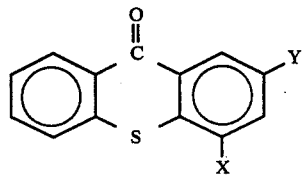

wherein X and Y may be the same or different, and represent a straight-chain or branched alkyl group having 1-12 carbon atoms with a proviso that sum of carbon atoms of alkyl groups X and Y is in the range of 3-15; a process for producing said compound; a process for hardening a photopolymerizable resin compound having an ethylenically unsaturated double bond which is radically crosslinkable or polymerizable using the above compound; and a photopolymerizable resin composition containing the same.

It has been known that thioxanthone compounds have excellent properties as photopolymerization initiators or sensitizers for photopolymerizable compounds having an ethylenically unsaturated double bond. However, those photopolymerization initiators and sensitizers have defects that they have a low solubility in organic solvents and photopolymerizable compounds and a poor compatibility with them in general. Those defects cause various troubles in practice. For example, unsubstituted thioxanthone has a poor solubility in and compatability with photopolymerizable compound and, therefore, even if it is dispersed finely in a resin using an organic solvent or the like, it crystallizes out during the storage for a long period of time. This phenomenon deteriorates essential functions of the photopolymerization initiators or sensitizers and exerts a bad influence on physical properties of a coated film after hardening. If they are used for the production of an ultraviolet-curing ink, the crystals deposit on rolls etc. and grow gradually to cause various troubles in the operation.

After intensive investigations made for the purposes of overcoming the above defects and producing thioxanthone compounds at a low cost on an industrial scale, the inventors have attained to the present invention.

The present invention is based on the discovery of the following important facts.

(1) When two alkyl groups are introduced into a thioxanthone nucleus, its solubility in organic solvents or photopolymerizable compounds and compatibility with them are improved remarkably.

(2) Among dialkylthioxanthone isomers, compounds of the above formula (I) have the highest hardening velocity.

(3) The dialkylthioxanthones have more excellent hardening velocity, solubility and storage stability in a dark place and less yellowing of the hardened film than those of monoalkylthioxanthones. (The films are hardened by irradiation with U.V. light. However, the films are colored yellow by the irradiation in some cases to make it impossible to obtain the intended, transparent or white films and also to degrade the commercial value of them. Thus, the yellowing should be prevented.)

(4) Among dialkylthioxanthone isomers, compounds of the above formula (I) can be obtained most easily in the highest yield.

(5) In the synthesis of monoalkylthioxanthones, the yield is greatly reduced as the alkyl chain thereof is elongated for the purpose of increasing the solubility. For example, a yield of 2-methylthioxanthone obtained by condensing dithiosalicyclic acid with toluene in sulfuric acid is about 80%, while yields of 2-isopropylthioxanthone and 2-t-butylthioxanthone are about 10% and less than 5%, respectively. Accordingly, they have been produced by other synthetic processes such as a complicated process disclosed in J. Oilcol. Chem. Assoc. 1978, 61, 258. On the other hand, m-dialkylthioxanthones produced from m-dialkylbenzenes in place of monoalkylbenzenes which are produced on an industrial basis at a high cost can be obtained in a high yield substantially irrespective of the length of the alkyl chains.

m-Dialkylthioxanthones of the formula (I) according to the present invention are new compounds. In formula (I), X and Y may be the same or different, and represents a straight-chain or branched alkyl group having 1-12 carbon atoms with a proviso that sum of carbon atoms of alkyl groups X and Y is in the range of 3-15.

As examples of alkyl groups X and Y, there may be mentioned methyl, ethyl, n-propyl, isopropyl, n-butyl, sec-butyl, tert-butyl, n-amyl, isoamyl, tert-amyl, n-hexyl, 1,1-dimethylbutyl, 1-ethyl-2-methylpropyl, 2-ethylbutyl, 1,3-dimethylbutyl, 4-methylpentyl, n-heptyl, 1-methylhexyl, 1-ethyl-1,2-dimethylpropyl, n-octyl, 2-ethylhexyl, 2,2,4-trimethylphentyl, n-nonyl, 1,3,5-trimethylhexyl, n-decyl, n-hendecyl, n-dodecyl and 2,2,4,4,6-pentamethylheptyl. Among these alkyl groups, methyl, ethyl, n-propyl and iso-propyl groups are most preferred.

Compounds of the above formula (I) of the present invention are prepared as follows:

Thiosalicyclic acid or dithiosalicyclic acid is reacted with a dialkylbenzene of the formula:

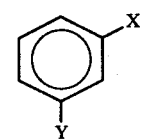

wherein X and Y have the same meaning as above in sulfuric acid to effect the condensation and ring closure.

The thus obtained compounds are represented by following formula:

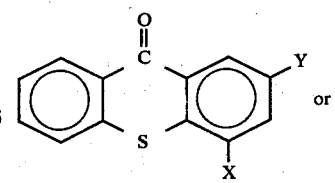 or 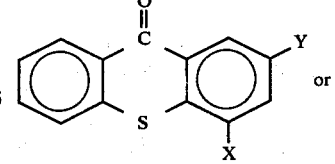

-continued

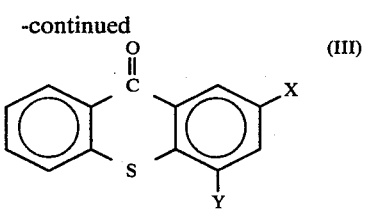
(III)

wherein X and Y have the same meaning as in the above formula (II).

As m-dialkylbenzenes of the above formula (II) used as the starting material of a compound of formula (I), there may be mentioned, for example, the following m-dialkylbenzenes obtained by mono- or di-alkylating ethylbenzene, toluene and benzene by Friedel-Crafts reaction: m-diethylbenzene, m-ethyltoluene, m-isopropyltoluene (m-cymene), m-propyltoluene, m-tert-butyltoluene, m-sec-butyltoluene, m-diisopropylbenzene, m-dipropylbenzene, m-isopropylethylbenzene, m-tert-butylethylbenzene, m-(1,1-dimethylpropyl)toluene, m-tert-butylisopropylbenzene, m-di-sec-butylbenzene, m-di-tert-butylbenzene, m-n-butyltoluene, m-tert-amylethylbenzene, m-n-dodecyltoluene, m-2-ethylbutyltoluene, m-2,2,4,4,6-pentamethylheptyltoluene, m-1,3,5-trimethylhexylethylbenzene, m-1,1-dimethylbutyltoluene and m-n-hendecyltoluene. Among these m-dialkylbenzene, m-diisopropylbenzene, m-diethylbenzene and m-isopropyltoluene are most preferable. The m-dialkylbenzene used may not always has a high purity. In some cases, a mixture of isomers of them having alkyl side chains of different carbon skeletons, a mixture of homologs having different carbon numbers or a mixture of o-, p- and m-isomers of them may be used. The mixture contains preferably at least 60% of m-isomer, since the o- and p-isomers have a low reaction velocity and they can be removed in the form of sulfonated compounds in the final stage of the reaction, and since, even if crystals of intended m-dialkylthioxanthone (2,4-dialkylthioxanthone) are contaminated with dialkylthioxanthones derived from o- and p-dialkylbenzenes, such as 1,4-, 1,2- and 2,3-dialkylthioxanthones, the crystals may be used as a photopolymerization initiator or sensitizer as such. m-Dialkylthioxanthones of formula (I) are obtained by various processes. For example, they may be produced by an ordinary process which eliminates water or hydrogen halide from the compound of the formula:

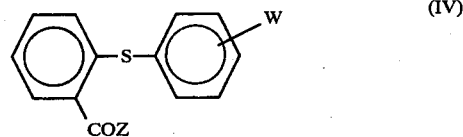
(IV)

wherein W represents alkyl, alkoxy, halogen or nitro and Z represents OH or halogen [J. Chem. Soc. 747 (1951); Collect. Czech. Chem. Commun. 32, 2161 (1967)]. However, this process is complicated and expensive and has problems when it is employed as an industrial process.

According to the process of the present invention, however, the above compounds can be prepared in an industrially advantageous way, since the condensation of thiosalicylic acid or dithiosalicylic acid with a m-dialkylbenzene in sulfuric acid and the ring closure can be effected in one bath.

The inventors have also found that high-purity dialkylthioxanthones can be obtained in a high yield only when m-dialkylbenzenes are used as the dialkylbenzenes. Namely, when o- or p-dialkylbenzenes are used, yield of the resulting dialkylthioxanthones is very poor.

In the condensation, ring-closure reaction according to the present invention, thiosalicylic acid or dithiosalicylic acid is added to sulfuric acid and then m-dialkylbenzene is added dropwise to the mixture under stirring at a low temperature, preferably −5° C. to 20° C. The order of the addition of thiosalicylic acid or dithiosalicylic acid and m-dialkylbenzene may be reversed. After completion of the addition, the whole is stirred for 2-20 h and then heated gradually to preferably 100°-150° C. In this step, the generation of sulfur dioxide is recognized. As the reaction proceeds, the reaction mixture is converted gradually into a dark red solution.

After cooling the reaction solution, it is poured onto ice-water. When the product in the solution is solid at room temperature, the reaction mixture is directly filtered to separate the crystals, which are then treated with an aqueous alkali solution to obtain generally white or light yellow crystals. When the product is liquid at room temperature, it is extracted from the ice-water with an organic solvent such as dichloroethane, ethyl acetate, benzene, toluene or chlorobenzene and the solvent layer is separated. The solvent is distilled out from the solvent layer by distillation or steam distillation and, if necessary, the residue is purified according to, for example, column chromatography to obtain an oily dialkylthioxanthone.

When an asymmetric m-dialkylbenzene such as m-cymene is used, two isomers of the above formulae (I) and (III) are obtained. Though the isomers can be separated from each other by, for example, recrystallization, they are used as a photopolymerization initiator or sensitizer as such without separation.

Sulfuric acid is used in an amount of preferably 3-20 parts by weight per one part by weight of thiosalicylic acid or dithiosalicylic acid. As for the concentration of sulfuric acid, fuming sulfuric acid of up to 10% or 50-100% sulfuric acid, preferably 80-96% sulfuric acid is used. Molar ratio of m-dialkylbenzene to thiosalicylic acid is 1-5/1 and that to dithiosalicylic acid is 2-10/1.

New dialkylthioxanthones of formula (I) of the present invention are added and used as sensitizers or photopolymerization initiators to a photopolymerizable compound which can be crosslinked or photopolymerized by exposure to active radiation.

Though dialkylthioxanthones may be used alone, it is preferred to use the same in combination with another photoactivator so as to accelerate the hardening under the irradiation with active radiation.

As preferred m-dialkylthioxanthones (2,4-dialkylthioxanthones) of formula (I) used as the photopolymerization initiator or sensitizer, there may be mentioned, for example, 2,4-diethylthioxanthone, 2,4-dimethylthioxanthone, 2,4-dipropylthioxanthone, 2,4-diisopropylthioxanthone, 2,4-di-tert-butylthioxanthone, 2,4-di-sec-butylthioxanthone, 2,4-ethylmethylthioxanthone, 2,4-methylethylthioxanthone, 2,4-methylisopropylthioxanthone, 2,4-isopropylmethylthioxanthone, 2,4-methyl-tert-butylthioxanthone, 2,4-tert-butylmethylthioxanthone, 2,4-ethylisopropylthioxanthone, 2,4-isopropylethylthioxanthone, 2-methyl-4-isopropylthioxanthone and 2-isopropyl-4-methylthioxanthone. Among them, 2,4-diethylthioxanthone, 2,4-diisopropylthioxanthone, 2-methyl-4-isopropylthioxanthone and 2-isopropyl-4-methylthioxanthone are particularly preferred.

As the photo-activator there may be mentioned, for example, active halogen-containing compounds such as chloromethylnaphthalene, and 2,6-bis(haloalkyl)-quinolines, and organic amines such as ethanolamine, diethanolamine, methyl diethanolamine, triethanolamine, dibutylamine, tributylamine, N-methyldiethanolamine, cyclohexylamine, morpholine, N-methylmorpholine, pyridine, quinoline, ethyl p-(N,N-dimethylamino)benzoate, isoamyl p-(N,N-dimethylamino)benzoate, p-(N,N-dimethylamino)benzaldehyde and Michler's ketone. Among them, particularly preferred are diethanolamine, methyl diethanolamine, triethanolamine and isoamyl p-(N,N-dimethylamino)benzoate. Dialkylthioxanthone of formula (I) according to the present invention is used in an amount in the range of 0.1–15 parts by weight, preferably 0.5–10 parts by weight, per 100 parts by weight of the photopolymerizable compound which will be shown below. Manner of producing photopolymerizable composition is preferably as follows: a compound of formula (I) is previously mixed with photoactivator and then dissolved or dispersed in a monomer or prepolymer of the photopolymerizable compound or in a suitable solvent such as dimethyl phthalate or, alternatively, the compound of formula (I) and photo-activator are respectively dissolved or dispersed as described in above and they are mixed before being used, then the resulting mixture is added to the photopolymerizable compound which will be described below in detail. The photo-activator which may be used in combination with the dialkylthioxanthone is used in an amount in the range of 0.1–20 parts by weight, preferably 0.2–4 parts by weight, per one part by weight of the dialkylthioxanthone.

Further, they may be used in combination with other, known photopolymerization initiators such as benzophenone, benzylbenzoic ether, dialkoxyacetophenones and benzyl ketal.

In addition, they may be used in combination with cationic photopolymerization initiators such as aryl halonium salts, arylsulfonium salts and ammonium salts disclosed in the specifications of Japanese Patent Publications Nos. 14277/1977, 14278/1977 and 14279/1977.

The photopolymerizable compounds which can be polymerized with the aid of the above-mentioned dialkylthioxanthones include, for example, monomers, oligomers, prepolymers, resins and mixtures of them which contain an ethylenically unsaturated double bond and which can be crosslinked or polymerized under irradiation with an active radiation. If necessary, they may contain additives such as an inhibitor, stabilizer, U.V. absorber, filler, pigment, dye and thixotropic agent.

As the monomers, oligomers, prepolymers and resins having active ethylenically unsaturated double bond, there may be mentioned, for example, acrylates or methacrylates of monohydric and polyhydric alcohols such as ethyl(meth)acrylate, butyl(meth)acrylate, ethylene glycol(meth)acrylate, trimethylolpropane tri(meth)acrylate, pentaerythritol tri(meth)acrylate, dipentaerythritol tetra(meth)acrylate, polyethylene glycol (meth)acrylate of a low molecular weight, polyester acrylates obtained by condensing polyhydric alcohols with monobasic acids or polybasic acids and then reacting the resulting polyester prepolymers with (meth)acrylic acid, polyurethane acrylates obtained by reacting polyols (polyester type or polyether type) with diisocyanato group-containing compounds and reacting the reaction product with (meth)acrylic acid, epoxy acrylates which are reaction products of epoxidized resins (such as bisphenol diglycidyl ethers, epoxidized oils and fats and epoxidized polybutadiene) with (meth)acrylic acid, silicon (meth)acrylates and melamine (meth)acrylates obtained from silicone oligomers and melamine oligomers in the same manner as above, and monomers and prepolymers having maleimido group such as copolymers of N-(Methacryloyloxyethyl)dimethylmaleimide and acrylic esters and copolymers of glycerol triglycidyl ether, α-phenylmaleimidoacetic acid and dimethylaminoethyl methacrylate.

As radiation sources used for the irradiation with active radiation, there may be mentioned various mercury lamps (low, high and ultra-high pressure mercury lamps), chemical halide lamps, xenone lamp, gallium lamp and thallium lamp.

The photopolymerizable resin composition comprising dialkylthioxanthone of formula (I), a photo-activator such as isoamyl p-(N,N-dimethylamino)benzoate and a colorant according to the present invention may be applied to a substrate made of, for example, a metal, mineral, glass, wood, paper, plastic, fabric or ceramics. The substrate having the coating film thus formed is placed on a conveyor which moves while it is irradiated with an active radiation from the above-mentioned lamp. The composition in this step is hardened generally in air and, as a matter of course, it may be hardened in an inert gas such as nitrogen.

If dialkylthioxanthone of formula (I) of the present invention having quite high solubility in and compatibility with the photopolymerizable compound is used, no crystallization or separation is observed at all during the storage for a long period of time. It is another advantage that a hardening velocity and hardening degree higher than practical standards can be obtained if the dialkylthioxanthone is incorporated with a photopolymerizable resin composition containing an inorganic or organic pigment generally used for the production of paints or inks. Particularly, good results are obtained in the production of opaque pigments containing titanium oxide or zinc oxide which was difficultly hardenable in the prior art.

The following examples will further illustrate the present invention.

EXAMPLE 1

142 g of 90% sulfuric acid was charged in a 300-ml four-neck flask. 34 g (0.25 mol) of m-diethylbenzene (b.p. 181°–182° C./760 mmHg, purity at least 98%) was added dropwise under stirring at 0° C. and then 24 g (0.0784 mol) of dithiosalicylic acid was added dropwise thereto. After stirring at a temperature of up to 5° C. for 3–4 h., the temperature was gradually elevated to 120°–130° C. in about 10 h and the whole was stirred under heating to said temperature for 1–2 h. The reaction liquid was converted gradually to a dark red solution. After cooling, it was poured onto about 800 g of ice-water. Crystals thus precipitated were filtered and thoroughly washed with water. The thus treated crystals were further treated with an aqueous sodium hydroxide solution to remove an alkali-soluble substance therefrom. After filtration followed by washing with water and drying, 2,4-diethylthioxanthone [m.p. 60° C., yield 35.1 g (84% based on dithiosalicylic acid; the same shall apply hereinafter)] of formula (I) was obtained as yellow crystals.

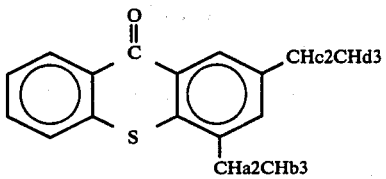

(A) Ms.s.: M+/e=268*1
(B) I.R. ($\nu_{c=o}$): 1630 cm$^{-1}$*2
(C) N.M.R.:
(Ha, Hc) 2.5–3.0. p.p.m.*3
4H(5)
(Hb, Hd) 1.15–1.45. p.p.m.
6H(4)
(D) Elementary analysis for S: Found 12.1%; Calcd. 11.9%.

*1Ms.s. means mass spectrum measured with LKB-900 (a product of Shimadzu Seisaku-sho) (the same shall apply hereinafter) at an ion source temperature of 310° C. at an ionization voltage of 70 eV).
*2I.R. means infrared absorption spectrum (the same shall apply hereinafter).
*3N.M.R.: Measured with Hitachi R-20B high-resolution nuclear magnetic resonance spectrometer, using CDCl$_3$ as solvent and tetramethylsilane (T.M.S.) as internal reference. Figures in the parentheses represent the number of peaks (the same shall apply in the following examples).

EXAMPLE 2

The reaction was carried out in the same manner as in Example 1 except that dithiosalicylic acid (0.0784 mol) and m-diisopropylbenzene (b.p. 203° C./760 mmHg, purity at least 98%) (0.25 mol) were used to obtain 2,4-diisopropylthioxanthone [m.p. 74°–76° C., 40.5 g (87% yield)].

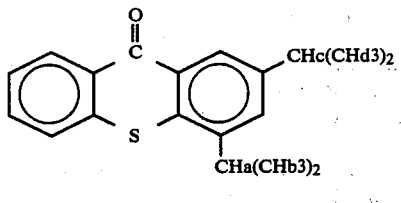

(A) Ms.s.: M+/e=296
(B) I.R. ($\nu_{c=o}$): 1630 cm$^{-1}$
(C) N.M.R.:
(Ha, Hc) 2.8–3.6 p.p.m.
2H(8)
(Hb, Hd) 1.25–1.4 p.p.m.
12H(4)
(D) Elementary analysis for S: Found 11.1%; Calcd. 10.81%.

EXAMPLE 3

The reaction was carried out in the same manner as in Example 2 except that dithiosalicylic acid was replaced with 24 g (0.157 mol) of thiosalicylic acid to obtain similar results to those obtained in Example 2.

EXAMPLE 4

The reaction was carried out in the same manner as in Example 1 except that 0.0784 mol of dithiosalicylic acid and 0.25 mol of m-isopropyltoluene (b.p. 176° C./760 mmHg, purity at least 98%) were used to obtain 35.5 g (85% yield) of m-isopropylmethylthioxanthone as light brown crystals. The product was a mixture of 78% of a compound of the following formula (4-a') (m.p. 97° C.) and 22% of a compound of the following formula (4-a'') (m.p. 134° C.). The compounds were separated from each other by recrystallization from ligroin solvent.

The structural formulae estimated were as follows:

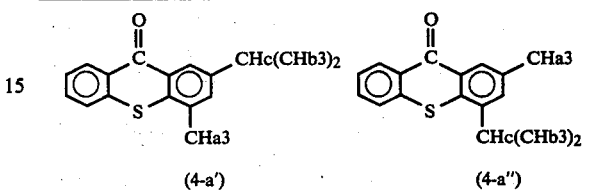

| | (4-a') | (4-a'') |
|---|---|---|
| (A) Ms.s.: | M+/e = 268 | M+/e = 268 |
| (B) I.R. ($\nu_{c=o}$): | 1630 cm$^{-1}$ | 1630 cm$^{-1}$ |
| (C) N.M.R.: | Ha: 2.5 p.p.m. 3H(1) | Ha: 2.48 p.p.m. 3H(1) |
| | Hb: 1.3 p.p.m. 6H(2) | Hb: 1.36 p.p.m. 6H(2) |
| | Hc: 3.0 p.p.m. 1H(4–5) | Hc: 3.4 p.p.m. 1H(4–5) |
| (D) Elementary analysis for S: | | |
| Found: | 12.0% | 12.1% |
| Calcd: | (11.9%) | (11.9%) |

EXAMPLE 5

The reaction was carried out in the same manner as in Example 1 except that 0.0784 mol of dithiosalicylic acid and 0.25 mol of m-tert-butyltoluene (b.p. 189° C./760 mmHg, purity at least 98%) were used to obtain m-tert-butylmethyl thioxanthone as light brown crystals (m.p. 134°–6° C., 36.2 g, 82% yield). Analytical results according to gas chromatography and mass spectrometry indicated that only one compound which had an M+/e of 282 was obtained and no isomer was obtained. A structural formula estimated was as follows:

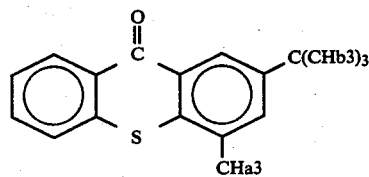

(A) Ms.s.: M+/e=282
(B) I.R. ($\nu_{c=o}$): 1630 cm$^{-1}$
(C) N.M.R.:
Ha; 2.5 p.p.m. 3H(1)
Hb; 1.38 p.p.m. 9H(1)
(D) Elementary analysis for S: Found 11.20%; Calcd. 11.34%.

EXAMPLES 6–13

The reaction was carried out according to the following reaction scheme in the same manner as in Example 1 using 0.08 mol of thiosalicylic acid and 0.15 mol of an m-dialkylbenzene of the following formula and a 2,4-dialkylthioxanthone shown in Table 1 was obtained.

TABLE I

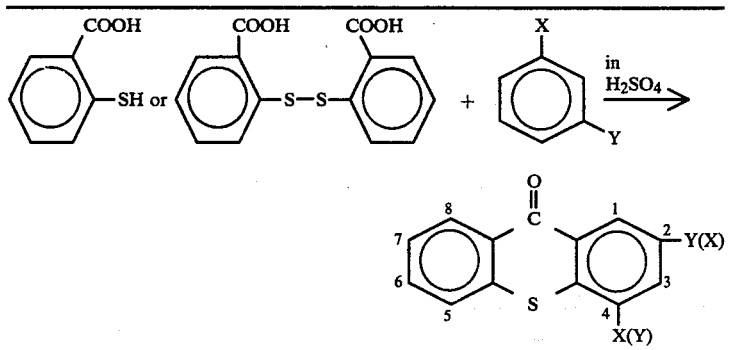

| Ex- | m-Dialkylbenzene | | 2,4-Dialkylthioxanthone | | | | I.R. |
|---|---|---|---|---|---|---|---|
| ample | X | Y | X | Y | Yield | $M^+/e$ | $(\nu_{c=o})$ |
| *6 | $CH_3$ | $C_2H_5$ | $CH_3$ | $C_2H_5$ | } 85% | 254 | $1630\ cm^{-1}$ |
|  |  |  | $C_2H_5$ | $CH_3$ |  | 254 | $1630\ cm^{-1}$ |
| *7 | $CH_3$ | $n$-$C_3H_7$ | $CH_3$ | $n$-$C_3H_7$ | } 85% | 268 | $1630\ cm^{-1}$ |
|  |  |  | $n$-$C_3H_7$ | $CH_3$ |  | 268 | $1630\ cm^{-1}$ |
| *8 | $C_2H_5$ | iso-$C_3H_7$ | $C_2H_5$ | iso-$C_3H_7$ | } 82% | 282 | $1630\ cm^{-1}$ |
|  |  |  | iso-$C_3H_7$ | $C_2H_5$ |  | 282 | $1630\ cm^{-1}$ |
| 9 | $n$-$C_3H_7$ | $n$-$C_3H_7$ | $n$-$C_3H_7$ | $n$-$C_3H_7$ | 81% | 296 | $1630\ cm^{-1}$ |
| 10 | $t$-$C_4H_9$ | $t$-$C_4H_9$ | $t$-$C_4H_9$ | $t$-$C_4H_9$ | 80% | 324 | $1630\ cm^{-1}$ |
| 11 | $CH_3$ | sec-$C_4H_9$ | $CH_3$ | sec-$C_4H_9$ | 81% | 282 | $1630\ cm^{-1}$ |
| 12 | $CH_3$ | $C_8H_{17}$ | $CH_3$ | $C_8H_{17}$ | 60% | 338 | $1630\ cm^{-1}$ |
| 13 | $CH_3$ | $C_{12}H_{25}$ | $CH_3$ | $C_{12}H_{25}$ | 52% | 394 | $1630\ cm^{-1}$ |

*Yield of a mixture of two isomers.

The above results indicate that when thiosalicylic acid or dithiosalicylic acid is reacted with an m-dialkylbenzene in sulfuric acid solvent, a corresponding 2,4-dialkylthioxanthone is obtained in a high yield.

EXAMPLES 14–22

A photopolymerizable resin composition was prepared according to the following recipe:

| | |
|---|---|
| Bisphenol A diglycidyl ether diacrylate | 55 parts by weight |
| Trimethylolpropane triacrylate | 45 parts by weight |
| Triethanolamine | 2.5 parts by weight |
| Photopolymerization initiator of formula (I) | 2.5 parts by weight |

-continued
(dialkylthioxanthone derivative)

The above photopolymerizable resin composition was applied to a glass plate in a thickness of 25µ and left 9 cm below a xenone lamp. The sensitivity was judged by measuring the time until the surface of the coated film ceases to be sticky (whether the coated film is sticky or not is judged by the touch with finger) under the continuous irradiation. The results are shown in Table II. In Table II, yellowing resistance and storage stability are also shown.

TABLE II

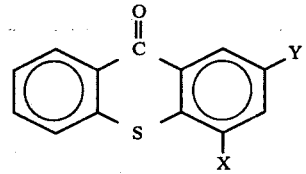

(I)

| Ex-ample | Number of Compound in above examples | X | Y | Hardening time (sec) | Yellowing resistance*[1] | Storage*[2] stability |
|---|---|---|---|---|---|---|
| 14 | 1 | $C_2H_5$ | $C_2H_5$ | 15 | A | A |
| 15 | 2 | iso-$C_3H_7$ | iso-$C_3H_7$ | 10 | A | A |
| 16 | 4 (4-a') | $CH_3$ | iso-$C_3H_7$ | 15 | A | A |
| 17 | 4 (4-a'') | iso-$C_3H_7$ | $CH_3$ | 20 | A | A |
| 18 | 5 | $CH_3$ | $t$-$C_4H_9$ | 15 | A | A |
| 19 | 6 | $CH_3$ } | $C_2H_5$ } | 20 | B | A |
| *3 |  | $C_2H_5$ | $CH_3$ |  |  |  |
| 20 | 10 | $t$-$C_4H_9$ | $t$-$C_4H_9$ | 25 | A | A |
| 21 | 12 | $CH_3$ | $C_8H_{17}$ | 25 | A | A |

TABLE II-continued

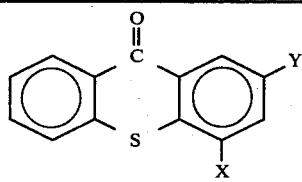
(I)

| Example | Number of Compound in above examples | X | Y | Hardening time (sec) | Yellowing resistance*1 | Storage*2 stability |
|---|---|---|---|---|---|---|
| 22 | 13 | $CH_3$ | $C_{12}H_{25}$ | 25 | A | A |

Irradiation device and conditions:
Xenon flashlamp (Stroboscope Typeps-240E; a product of Eagle Shoji Co.), Discharge tube input: 0.445 × 50 J/sec (Voltage 1300 V)
Lamp length: 15 cm
*1Yellowing resistance in the above table was estimated visually from the state of the coating film after the irradiation.
    A: Only slight yellowing
    B: Clear yellowing
    C: Remarkable yellowing.
*2Storage stability was estimated from the state of gelation of the above-mentioned photopolymerizable resin composition after leaving the same in a glass bottle at 120° C. for 12 h.
    A: Clear gelation was not recognized.
    B: Partial gelation was recognized on the surface and the vessel walls.
    C: The composition gelled substantially completely.
*3The isomer mixture in Preparation Example 6 was used.

The above results indicate that 2,4-dialkylthioxanthones of formula (I) of the present invention have excellent sensitivity, yellowing resistance and storage stability. This fact will be apparent from the following Table III.

The effects of m-dialkylthioxanthones will be apparent when compared with those of o- or p-dialkylthioxanthones, monoalkylthioxanthones and unsubstituted thioxanthones.

CONTROL EXAMPLE 1

TABLE III

| o- or p-dialkylthioxanthone or monoalkylthioxanthone | Hardening time (sec) | Yellowing resistance | Storage stability |
|---|---|---|---|
| Mixture of 1,2-, 2,3- and 3,4- diethylthioxanthones | >60 | — | A |
| 1,4-Diethylthioxanthone | 50 | A | A |
| 1-Methyl-2-ethylthioxanthone | >60 | — | A |
| 1-Methyl-4-ethylthioxanthone | 50 | B | A |
| Mixture of 1,2-, 2,3- and 3,4- diisopropylthioxanthones | >60 | — | A |
| 1,4-Diisopropylthioxanthone | 50 | A | A |

TABLE III-continued

| o- or p-dialkylthioxanthone or monoalkylthioxanthone | Hardening time (sec) | Yellowing resistance | Storage stability |
|---|---|---|---|
| 1-Ethyl-2-isopropylthioxanthone | 50 | A | A |
| 1,4-Dimethylthioxanthone | 40 | B | A |
| Methylthioxanthone | 40 | C | B |
| Ethylthioxanthone | 40 | C | B |
| Isopropylthioxanthone | 20 | B | B |
| Thioxanthone | >60 | — | A |

*Yellowing resistance and storage stability were estimated on the same criteria as in Table II.

It is apparent from Table IV that the compounds of the present invention have more excellent solubility in organic solvents than those of known thioxanthone compounds.

TABLE IV

| | Solubility (g/solvent 100 ml) | | | | | | |
|---|---|---|---|---|---|---|---|
| Compound | 1,2-Dichloroethane | 1,2-Dichloropropane | Toluene | Acetone | Ethanol | Methanol | Ethyl acetate |
| 1 | 1.1 | <0.5 | <0.5 | <0.5 | <0.5 | <0.5 | 0.5 |
| 2 | 16.6 | 7.7 | 5.5 | 3.0 | <1.0 | <1.0 | 2.9 |
| 3 | >50.0 | >50.0 | >50.0 | 30.0 | 3.6 | 3.3 | 30.0 |
| 4 | >50.0 | >50.0 | >50.0 | >40.0 | 9.0 | 6.0 | >50.0 |

*Compound (1): thioxanthone (known)
Compound (2): 2-methylthioxanthone (known)
Compound (3): 2-isopropylthioxanthone (known)
Compound (4): 2,4-diisopropylthioxanthone (present invention).

The results shown in Tables II, III and IV indicate that 2,4-dialkylthioxanthones are excellent photopolymerization initiators.

EXAMPLES 23-28

The following photopolymerizable resin compositions (A) and (B) were prepared. Each of the compositions was applied to an aluminum plate in a thickness of 25μ. The aluminum plate was placed on a belt conveyer moving 20 cm below an 80 W/cm high-pressure mercury lamp at a speed of 18 m/min. Relationship between the number of passage times and physical properties of the coating film was examined to obtain the results shown in Table V.

Photopolymerizable resin compositions

| (A) | Carbon black-containing composition: | |
|---|---|---|
| | Epoxy acrylate resin (Shell DRH 303) | 59.3 parts by weight |
| | Trimethylolpropane triacrylate | 20.4 parts by weight |
| | Hexanediol diacrylate | 14.8 parts by weight |
| | Carbon black | 2.5 parts by weight |
| | Methyldiethanolamine | 2.0 parts by weight |
| | Photopolymerization initiator of formula (I) (dialkylthioxanthone) | 1.0 parts by weight |
| (B) | Titanium oxide-containing composition: | |
| | Urethane acrylate resin (Thiokol Uvithane 788) | 35.8 parts by weight |
| | Trimethylolpropane triacrylate | 9.4 parts by weight |
| | Butyl acrylate | 18.8 parts by weight |
| | Vinylpyrrolidone | 9.4 parts by weight |
| | Titanium oxide (rutile type) | 24.4 parts by weight |
| | Methyldiethanolamine | 1.5 parts by weight |
| | Photopolymerization initiator of formula (I) (dialkylthioxanthone) | 0.75 parts by weight |

TABLE V

| Example | Photopoly-merizable composition | Polym. initiator of Formula (1)*1 | Pencil hardness after passing*2 | | | | | Yellowing*3 resistance |
|---|---|---|---|---|---|---|---|---|
| | | | Once | Twice | 3 times | 4 times | 5 times | 6 times | |
| 23 | (A) | (a) | F | — | 3H | — | 6H | — | — |
| 24 | (B) | (a) | — | HB | — | F | — | 3H | A |
| 25 | (A) | (b) | F | — | 4H | — | 6H or higher | — | — |
| 26 | (B) | (b) | — | HB | — | F | — | 4H | A |
| 27 | (A) | (c) | F | — | 3H | — | 6H | — | — |
| 28 | (B) | (c) | — | HB | — | F | — | 3H | A |

*1Polymerization initiators of formula (I) were as follows:
(a) 2,4-Diethylthioxanthone
(b) 2,4-Diisopropylthioxanthone
(c) 2-Isopropyl-4-methylthioxanthone
*2Pencil hardness was determined according to JIS-K 5400 6, 14.
*3Yellowing resistance was estimated based on the same criteria as in Table II.

The above results indicate that when the compounds of the present invention are used in pigment-containing systems, coating films having excellent strengths can be obtained.

EXAMPLE 29

16 Parts of diglycerol triglycidyl ether, 23 parts by weight of α-phenylmaleimidoacetic acid, 0.2 part by weight of dimethylaminoethyl methacrylate and 40 parts by weight of butyl acetate were reacted together at 90°-100° C. for 2 h to obtain a trifunctional photopolymerizable resin in which α-phenylmaleimidoacetic acid was added to substantially all glycidyl groups. 2.5 Parts by weight of 2,4-diisopropylthioxanthone of the present invention was added to 100 parts by weight of the above resin and the whole was kneaded thoroughly and applied onto a glass plate in a thickness of 50μ. The coating film on the glass was irradiated with a light using an 80 W/cm high-pressure mercury lamp placed at a distance of 10 cm for 20 sec to obtain a coating film insoluble in dichloroethane or acetone. In case 2,4-diisopropylthioxanthone was not added, the film was not hardened even after 60 min. This fact suggests that 2,4-diisopropylthioxanthone is an excellent sensitizer.

What is claimed is:

1. A dialkylthoxanthone compound of the general formula:

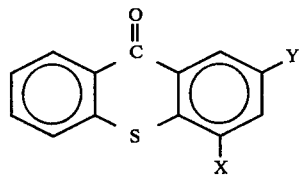

(I)′ wherein X and Y may be the same or different, and represent a straight-chain or branched alkyl group having 1–12 carbon atoms with a proviso that sum of carbon atoms of alkyl groups X and Y is in the range of 3–15.

2. A dialkylthioxanthone compound according to claim 1 wherein X and Y are isopropyl.

3. A dialkylthioxanthone compound according to claim 1 wherein X and Y are ethyl.

4. A dialkylthioxanthone compound according to claim 1 wherein one of X and Y is methyl and the other is isopropyl.

* * * * *

UNITED STATES PATENT AND TRADEMARK OFFICE
CERTIFICATE OF CORRECTION

PATENT NO. : 4,450,279
DATED : May 22, 1984
INVENTOR(S) : Tsutomu Shirosaki & Seiki Fukunaga It is certified that error appears in the above-identified patent and that said Letters Patent is hereby corrected as shown below:

On the face of the patent, Item [73] Assignee:

change "Nippon, Kayaku, Kabushiki, Kaisha,"

to

--Nippon Kayaku Kabushiki Kaisha,--

Signed and Sealed this

Twenty-sixth Day of February 1985

[SEAL]

Attest:

DONALD J. QUIGG

*Attesting Officer*     *Acting Commissioner of Patents and Trademarks*